US011291820B2

(12) United States Patent
Shin et al.

(10) Patent No.: US 11,291,820 B2
(45) Date of Patent: Apr. 5, 2022

(54) VALVE ASSEMBLY WITH SEALING CAPABILITY FOR INSTRUMENTS AND/OR GUIDE WIRES FOR USE AS ACCESS/TOOL PORT

(71) Applicant: INNOVHEART S.R.L., Milan (IT)

(72) Inventors: Dong Ik Shin, Poway, CA (US); Giovanni Righini, Gland (CH); Cindy Trinh, Moreno Valley, CA (US)

(73) Assignee: INNOVHEART S.R.L., Milan (IT)

( * ) Notice: Subject to any disclaimer, the term of this patent is extended or adjusted under 35 U.S.C. 154(b) by 18 days.

(21) Appl. No.: 16/633,894

(22) PCT Filed: Jul. 24, 2018

(86) PCT No.: PCT/IB2018/055484
§ 371 (c)(1),
(2) Date: Jan. 24, 2020

(87) PCT Pub. No.: WO2019/021164
PCT Pub. Date: Jan. 31, 2019

(65) Prior Publication Data
US 2021/0085948 A1 Mar. 25, 2021

Related U.S. Application Data

(60) Provisional application No. 62/536,199, filed on Jul. 24, 2017.

(51) Int. Cl.
*A61M 39/06* (2006.01)
*A61B 17/34* (2006.01)

(52) U.S. Cl.
CPC .......... *A61M 39/06* (2013.01); *A61B 17/3423* (2013.01); *A61B 17/3462* (2013.01);
(Continued)

(58) Field of Classification Search
CPC .......... A61M 39/06; A61M 2039/0626; A61B 17/3423; A61B 17/3462;
(Continued)

(56) References Cited

U.S. PATENT DOCUMENTS 3,538,917 A * 11/1970 Selker .................. A61B 17/122
251/5
5,071,411 A * 12/1991 Hillstead ............ A61B 17/3462
604/9

(Continued)

FOREIGN PATENT DOCUMENTS

DE 4312147 A1 10/1993
WO 2012/063228 A1 5/2012
(Continued)

OTHER PUBLICATIONS

International Search Report for corresponding application No. PCT/IB/2018/055484, dated Oct. 10, 2018 (3 pages).
(Continued)

*Primary Examiner* — Theodore J Stigell
(74) *Attorney, Agent, or Firm* — Flynn Thiel, P.C.

(57) ABSTRACT

A valve assembly for instruments and/or guide wires for use as access/tool port includes a cannula attached to a valve housing with a through hole. Elastic valve members are housed in the valve housing for sealing the through hole either when no device is inserted, or when a specific device with a compatible cross section is inserted. A further sealing arrangement is housed in the valve housing. The further sealing arrangement is extendable within the valve housing to selectively reduce the width of the through hole from a non-sealed configuration where one generic device or a group of generic devices, not necessarily having the same size and/or shape, can be inserted into and/or removed from the through hole, to a sealed configuration where the sealing arrangement seals the through hole with the generic device (Continued)

or the group of generic devices inserted into the through hole.

10 Claims, 9 Drawing Sheets

(52) U.S. Cl.
CPC ............... *A61B 2017/3464* (2013.01); *A61B 2017/3466* (2013.01); *A61B 2017/3486* (2013.01); *A61M 2039/0626* (2013.01)

(58) Field of Classification Search
CPC .... A61B 2017/3464; A61B 2017/3466; A61B 2017/3486; A61B 2017/00557; A61B 17/3421; A61B 17/3431
See application file for complete search history.

(56) References Cited

U.S. PATENT DOCUMENTS

| | | | |
|---|---|---|---|
| 5,423,848 A | | 6/1995 | Washizuka et al. |
| 5,782,817 A | * | 7/1998 | Franzel ............ A61M 39/0606 251/5 |
| 5,997,515 A | * | 12/1999 | de la Torre ........ A61B 17/3417 604/246 |
| 6,276,661 B1 | * | 8/2001 | Laird ................ A61B 17/3462 137/317 |
| 8,317,690 B2 | * | 11/2012 | Ransden ............ A61B 17/3468 600/206 |
| 2010/0312060 A1 | * | 12/2010 | Widenhouse ..... A61M 39/0693 604/167.01 |

FOREIGN PATENT DOCUMENTS

| | | |
|---|---|---|
| WO | 2014/080338 A1 | 5/2014 |
| WO | 2014/080339 A1 | 5/2014 |
| WO | 2015/118464 A1 | 8/2015 |
| WO | 2016/168226 A1 | 10/2016 |

OTHER PUBLICATIONS

Written Opinion of the International Searching Authority for corresponding application No. PCT/IB2018/055484, dated Oct. 10, 2018 (5 pages).

* cited by examiner

Fig. 1

KNOWN ART

Fig. 17 understand # VALVE ASSEMBLY WITH SEALING CAPABILITY FOR INSTRUMENTS AND/OR GUIDE WIRES FOR USE AS ACCESS/TOOL PORT

CROSS-REFERENCE TO RELATED APPLICATIONS

This is the National Stage of International Application No. PCT/IB2018/055484, filed Jul. 24, 2018, which claims the benefit of U.S. Provisional Application No. 62/536,199, filed Jul. 24, 2017.

FIELD OF INVENTION

The present invention is in the technical field of medical devices. It relates to a valve assembly. More specifically, the invention relates to a valve assembly for permitting the introduction of therapeutic instruments, such as a catheter, and/or guide wires into a patient's body while providing a substantial seal against leakage of fluids and gasses through the valve assembly.

The invention has been developed with particular reference to a valve assembly for use as access/tool port arrangement to help facilitate techniques and devices for cardiovascular valve replacement, repair, or any other medical treatment where access to body is required without severe bleeding during inserting and/or exchanging the devices.

TECHNICAL BACKGROUND

Historically, the corrective treatment of dysfunctions related to the main cardiac pathologies has been associated with surgical procedures which are highly invasive for the patient and are frequently accompanied by high intraoperative mortality. A typical example of these procedures is that of the replacement or repair of malfunctioning heart valves. In such a case, the surgical procedure generally includes the surgical opening of the chest, the emptying of the heart, requiring extracorporeal circulation in what are known as heart-lung machines, and the surgical opening of the heart itself to provide direct access to the malfunctioning heart valve. The treatment of the valve requires either its reconstruction by surgical methods, often with the support of prosthetic devices such as annuloplasty rings, or its complete removal and replacement with an artificial prosthesis. Clearly, this procedure, although necessary for survival, represents a serious trauma for the patient. In some cases, the patient's general condition, for example old age and the presence of concomitant pathologies, means that the risks of mortality associated with these surgical procedures are so high as to be considered unacceptable. Consequently the patient must be denied surgical treatment, and thus loses his access to a therapy which is essential to the improvement of his quality of life and any expectation of long-term survival.

Recently, methods of treatment and correction of cardiac pathologies have been developed with the aim of providing the same efficacy as surgical treatment, but with a drastic reduction in the invasiveness of the procedure, thereby greatly decreasing the incidence of intra- and post-operative complications and almost completely eliminating discomfort for the patient. These methods are essentially based on the use of catheters, from which the general term "transcatheter methods" is derived, as well as endoscopic instruments and special prosthetic devices. These devices may be reduced in their overall dimensions during their introduction into the cardiac cavities via access/tool ports with low invasiveness (for example, transfemoral, transvenous, transapical and other accesses), and then deployed in their operating configuration when the implantation site has been reached. Specifically, the artificial prosthesis is radially compressed; a guidance system, generally a catheter, guides the prosthesis as far as the implantation site thereof; once the prosthesis has been correctly positioned, it is released by the guidance system and expands, for example, owing to resilient return or by a balloon positioned therein being inflated, so as to recover the operating dimensions thereof.

These methods usually require a set of devices, ancillary to the procedure, which are intended to make the procedure safer, faster and more effective. For example, in case of a transcatheter implantation of an aortic valve prosthesis, it is normal practice for the first step of the procedure to be that of crossing the malfunctioning valve with a guide wire, usually metallic, this guide wire being introduced through the access which is subsequently used for the implantation system, after which the catheter which carries the prosthesis itself to the implantation site is made to slide along the guide wire. This preliminary positioning of the guide wire makes the catheter navigation more reliable and effective, while reducing the duration and risk of the procedure.

In the field of the treatment of malfunctioning heart valves by transcatheter methods, treatments for restoring valve function characterized by low invasiveness are under development not only for the aortic valve, but also for the mitral valve. For example, WO 2012/063228, WO 2014/080339 and WO 2015/118464 describe prosthetic systems capable of replacing the function of an atrioventricular heart valve, in other words a mitral or a tricuspid valve. In these systems, a substantially annular structure is deployed around the native valve, surrounding the whole valvular and subvalvular apparatus.

WO 2014/080338 describes a device for the deployment of a system of guide wires within a cardiac chamber. The device comprises an introducer catheter within which guide catheters are positioned. These guide catheters convey and direct the distal ends of respective guide wires, placed within the guide catheters, towards a capture member of a capture system which can be selectively drawn out of and retracted into the introducer catheter. The capture member is adapted to capture the distal ends of the guide wires so as to draw them into the introducer catheter. Said WO 2014/080338 also describes a procedure for implanting a prosthetic system for replacement of the mitral valve by a transcatheter technique and transapical route. The procedure comprises a preparatory step involving the introduction in the left ventricle of two guide wires which are positioned so as to surround the mitral valve.

It is therefore evident that with the advent of Transcatheter Aortic Valve Replacement (TAVR) and Transcatheter Mitral Valve Replacement (TMVR), the need to access the body via Apical Puncture or via Vascular access has increased.

At present there are known devices including a valve assembly that can seal the access/tool port either when there is nothing in its through hole, or when something that is large enough is introduced therein to work against the secondary seal. A typical example of such a valve assembly makes use of a duckbill valve.

A major drawback of the known valve assemblies is that the seal is configured to properly seal the through hole of the access/tool port against a single, often relatively large device, such as a big catheter or cannula. They however are less effective to seal the through hole when there are single or multiple guide wires which have a relatively small diameter compared to the diameter of the through hole.

SUMMARY OF THE INVENTION

One aim of the present invention is that of providing a valve assembly with sealing capability for instruments and/or guide wires for use as access/tool port, which solves the problem of the known art. In particular, it is an aim of the present invention to allow sealing/hemostasis of the valve assembly when there are in it single or even multiple tools of a relatively small diameter, such as guide wires (GW), catheters, sheaths or tubing for the guide wires. It is another aim of the invention to allow sealing/hemostasis of the valve assembly both when smaller diameter tools, such as guide wires or the like, and when larger diameter tools or devices are introduced in the through hole of the valve assembly, i.e. the access/tool port. In practice, the present invention aims to achieve a good sealing in every situation, that is, not only when there is nothing inserted in the through hole, but also irrespective of the size, shape, diameter and number of tools introduced in the through hole of the valve assembly. It is also an aim of the present invention to provide a valve assembly of the type indicated above, which is simple, effective, reliable, easy to use and relatively affordable.

According to an aspect, a valve assembly for use as a medical access/tool port that uses at least one balloon, particularly an inflatable balloon as a sealing element is provided. According to a particular aspect, the valve assembly uses multiple inflatable balloons. According to another particular aspect, the valve assembly uses the inflatable balloon or balloons in addition to one or more sealing valves to compensate or adjust for the diameter when larger or smaller devices are inserted and/or removed. These smaller devices can be single or multiple smaller guide wires or catheters or the like, like sheaths or tubing.

The invention addresses the increased need for a device that allows hemostasis during insertion and exchange of tools or catheters in the body. At times, single or multiple guide wires or catheters are left in place while the next device is inserted. The provision of large diameter balloon(s) enables the closure of fluid passage in the access/tool port so that an effective hemostasis is achieved. By means of the balloon(s) a significant increase of the hemostasis capability is obtained.

According to another aspect, a deformable liner of the through hole is provided which further increases the hemostasis. According to a special aspect, the liner is a tubular liner of a soft material. The deformable liner increases the effectiveness of the sealing, because guide wires, catheters or the like can be pressed against the liner by the inflatable balloon(s). The deformable liner, and particularly the softer material thereof, fills the interstices between the guide wires. According to a particular aspect, the deformable liner comprises soft or deformable projections or ribs. According to yet another particular aspect, the tubular liner has multiple circular ribs spaced axially along the length of the tubular liner. These projections or ribs will fill the interstices or gaps between the guide wires or catheters, along part of their circumferences.

In substance, several embodiments are described which incorporate several aspects pertaining to the present invention.

According to a particular aspect, a valve assembly with sealing capability for instruments and/or guide wires for use as access/tool port is provided, comprising a cannula attached to a valve housing with a through hole. A first elastic valve member, typically a duckbill valve, is housed in the valve housing for sealing the through hole when no device is inserted into it. A second elastic valve member is housed in the valve housing for sealing the through hole when a device having a compatible (in shape and dimensions) cross section is inserted into it. A further sealing arrangement is housed in the valve housing. The further sealing arrangement is extendable within the valve housing so as to selectively reduce the width of the through hole. The width of the through hole is reduced from a non-sealed configuration where one or more devices can be inserted into and/or removed from the through hole, to a sealed configuration where the sealing arrangement tightly conforms to the periphery of one generic device or a group of generic devices, not necessarily having the same size and/or shape, inserted into the through hole. Advantageously, such a valve assembly can avoid leaking in several conditions, irrespective of the diameter, number, size and shape of the cross section of the devices inserted into the through hole, and also, if needed, when no device is inserted into it.

In a particular embodiment, the further sealing arrangement comprises one or more inflatable balloons. The use of inflatable balloons allows for an affordable, simple and reliable valve assembly.

In a particular embodiment, the valve assembly comprises a soft liner which cooperates with a wall of an inflatable balloon to close and seal the gaps around the periphery of one generic device or a group of generic devices, not necessarily having the same size and/or shape. The soft liner is easy to produce, and provides an important enhancement to the sealing capability of the valve assembly even for low/medium pressures of the inflatable balloon.

In a particular embodiment, the soft liner comprises soft annular ribs distributed along the length of the liner, on an inner surface thereof. This configuration contributes to the effective sealing of the through hole, because the soft ribs or rings distributed along the length of the liner provide a series of barriers which all together improve the sealing effect around the periphery of the devices, e.g. guide wires/tubing inserted in the valve assembly.

According to another particular embodiment, the one or more inflatable balloons have tails. A first tail communicates with the interior of the balloon to inflate/deflate it. A second tail is used to anchor the balloon to the valve housing. The tails are formed during the moulding of the balloons and are adapted for use within the valve assembly.

According to another particular embodiment, the tails are eccentric with respect to a longitudinal axis of the balloon. The eccentricity allows for a more compact valve assembly, which uses less space to achieve the same effects and therefore is less invasive in a body.

According to a different embodiment, the balloon is an elastic balloon which is assembled airtight to the valve housing. The elastic balloon is inflatable towards the centre of the valve housing so as to close and seal the gaps around the periphery of one generic device or a group of generic devices, not necessarily having the same size and/or shape, which are then grouped substantially at the centre of the valve housing.

According to a different embodiment, the further sealing arrangement comprises a flexible iris tubing inserted into the valve housing. The ends of the flexible iris tubing are connected to respective iris rings which are rotatable with respect to each other about the longitudinal axis of the flexible iris tubing. The rotation of the iris rings allows the progressive shrinking of the flexible iris tubing towards the centre of the valve housing to close and seal the gaps around the periphery of one generic device or a group of generic devices, not necessarily having the same size and/or shape, which are thus grouped substantially at the centre of the valve housing. This arrangement allows an effective seal to be achieved without the need to inflate a balloon, but rather provoke the expansion of the flexible iris tubing, and its consequent shrinking of the through hole, by means of a simple mechanical operation which can be directed by the outside of the valve assembly, for example by means of the cannula.

BRIEF DESCRIPTION OF THE DRAWINGS

These and other features and advantages will be evident from the following detailed description of preferred embodiments of the invention, with reference to the attached drawings, given by view of non limiting examples, in which.

DETAILED DESCRIPTION

Definitions

As used herein, the term "access port" or "tool port" or "access/tool port" is a system comprising components which can be positioned inside the body to provide entry into the body with different types of devices without causing undue damage to the tissue.

As used herein, the term "cannula" can generally refer to a long round member assembled to the distal part of the access port. This is the part that enters the body and mainly contacts the tissue and this is typically, although not limiting, tied around with a suture.

As used herein, the term "duckbill valve" can generally refer to a valve made from an elastomer that provides the main sealing when there are no devices going through the cannula and the valve assembly.

As used herein, the term "balloon" can generally refer to a flexible pressure vessel that can be inflated to make a seal in a various internal shapes.

As used herein, the term "Guide wire(s)/tubing" or "catheter" can generally refer to an elongated member that goes through the cannula and the other valves of the valve assembly that can cause disruption in sealing of device, and against which the sealing of the present device is effective.

As used herein, the term "Liner" can generally refer to a cylindrical tubular member preferably made of elastomer to improve sealing when used in conjunction with a balloon.

Figure 1:
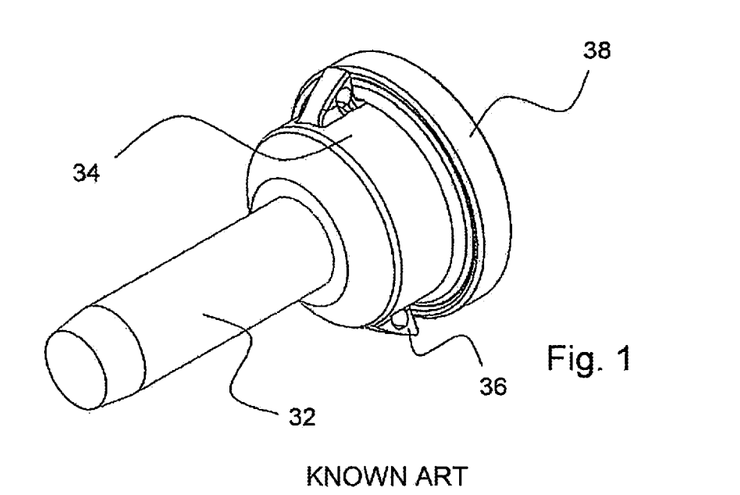
FIG. 1 shows a valve assembly of the known art, having a standard dual seal system used to access the body.

Referring to FIG. 1, a valve assembly of the known art is shown, having a standard dual seal system used to access the body. This figure shows a cannula 32 attached to a valve housing 34 containing a duckbill valve (not shown). The valve housing is closed by a cap 38 with a central hole. These three items typically compose a standard access port. Suture tabs 36 are used for better anchoring of the access port to the body.

Figure 2:
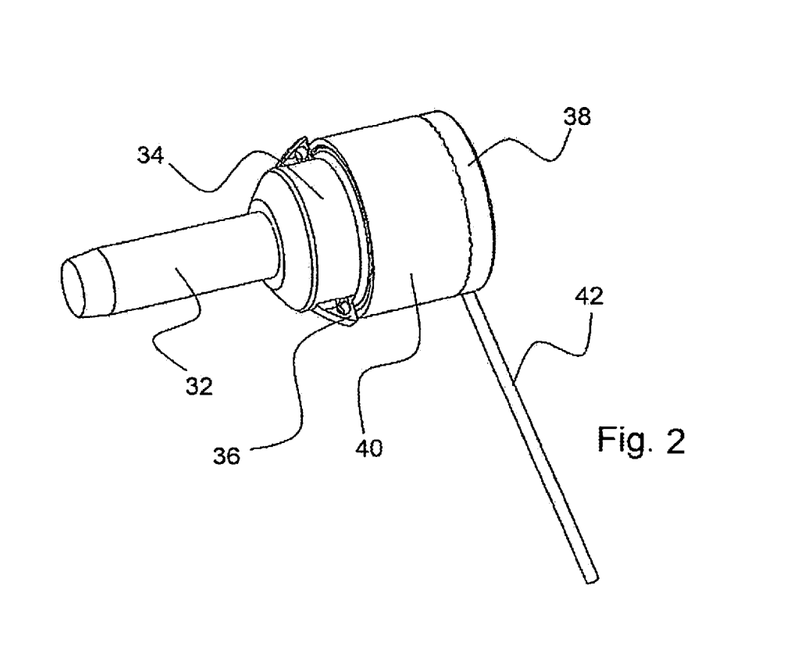
FIG. 2 is an illustration of a first embodiment of a valve assembly incorporating aspects of the invention, including a balloon assembled in a housing with an inflation tubing.
Figure 3:
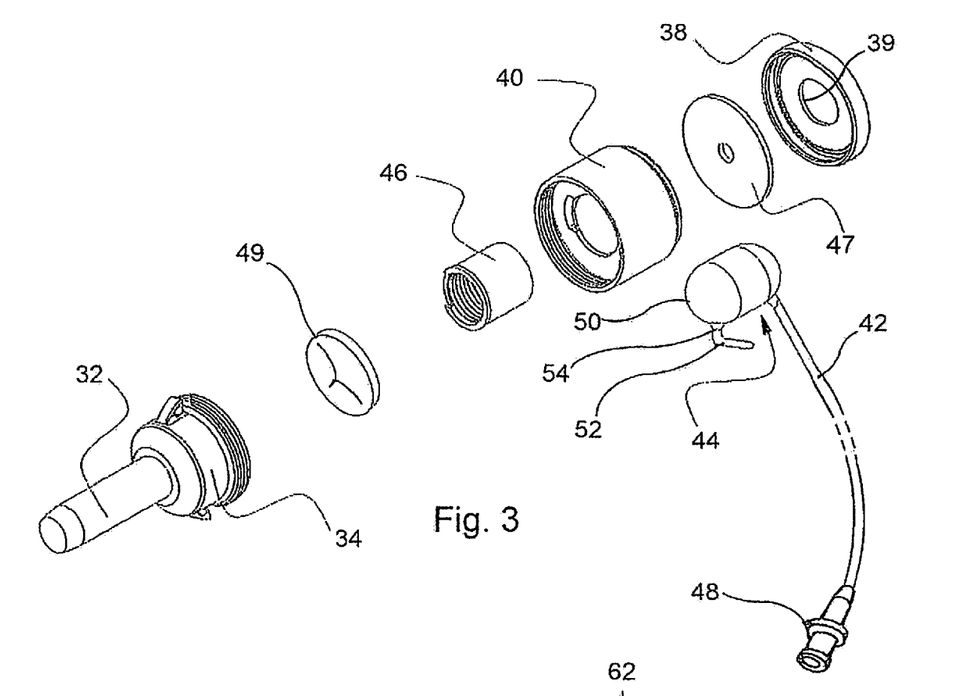
FIG. 3 is an exploded view of the valve assembly of FIG. 2.

Referring to FIGS. 2 and 3, a preferred embodiment of a valve assembly including aspects of the present invention is shown. The valve assembly includes the cannula 32 attached to the valve housing 34 containing the duckbill valve 49 (FIG. 3). The valve housing 34 is closed by the cap 38 with the central hole 39. Additionally, the valve assembly comprises a balloon housing 40. The balloon housing 40 is adapted to contain a balloon 44. The balloon housing 40 allows the balloon 44 to be assembled onto the access port. The balloon 44 has an interior chamber 44a (shown partially and in dotted lines in FIG. 7) defined by an inner surface 44b (also shown in dotted lines in FIG. 7) of the balloon 44. The balloon 44 can be inflated and deflated. Preferably, the balloon 44 can be inflated and deflated using a balloon round tail 42. A balloon inflation/deflation luer 48 is attached to the balloon round tail 42 or an extension thereof.

The balloon housing 40 is lined with a liner 46. The liner 40 is preferably a soft liner, more preferably a ribbed silicone liner. The balloon 44 is assembled inside the ribbed silicone liner 46, which in turn is inside the balloon housing 40. The balloon housing 40 is assembled to cannula 32/duckbill housing 34 at the distal side. At the opposite side, a large seal 47, preferably a silicone seal, is assembled between the proximal end of the balloon housing 40 and the proximal seal cap 38. The seal cap 38 is preferably a ribbed seal cap. The large seal 47 allows the sealing of the access port when larger diameters tools are inserted therein.

The seals of the valve assembly can be moulded from a low durometer silicone. The liner can, however, be made from variety of elastomers.

In a preferred but non limiting configuration, the main body 50 of the balloon 44 is cylindrical when pressurized. One of the balloon tails is a flat sealed tail 52 and the transition from the balloon main body 50 is a balloon flat curved tail 54. The design of such a balloon flat tails 52, 54 allows more efficient use of space in the balloon housing 40. The tails of the balloon, both the round tail 42 and the flat tails 52, 54 are preferably eccentric with respect to a main longitudinal axis of the main body 50 of the balloon 44. Having the tails eccentric from the main balloon body 50 allows a single balloon to be efficiently assembled into the balloon housing 40. However, a standard shaped balloon with symmetrical tails and cones can also be used.

Figure 4:
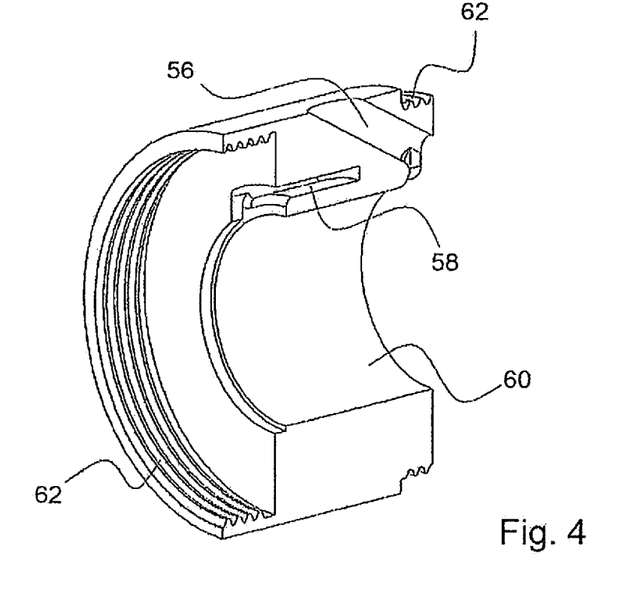
FIG. 4 is an enlarged, cross-sectional perspective view of a balloon housing of the valve assembly of FIGS. 2 and 3, without any liner.

As can be seen in FIG. 4, the housing 40 provides a balloon housing round tail exit 56 for the balloon round tail 42. The balloon housing round tail exit 56 is angled and recessed from the balloon housing wall to provide a better sealing surface for the large silicone seal 47. A bonding cavity 58 for the flat tail 52 is matched in shape to the balloon flat tail 52 and is recessed as well to allow the duckbill valve 49 to seal against a flatter surface of the balloon housing 40. The balloon housing threads 62 allow easier assembly and disassembly of the valve assembly components. However, the components can be joined together in ways other than by a threaded connection, that is by welding, adhesive bonding or use of locking tabs, and any other means which are known the those skilled in the art of assembly.

Figure 5:
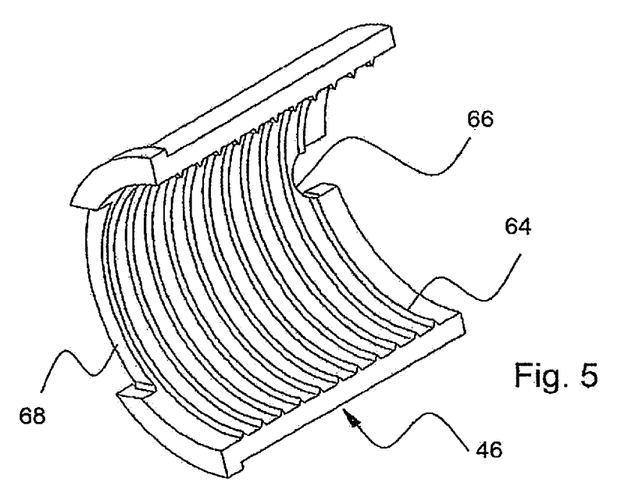
FIG. 5 is an enlarged, cross-sectional view of a ribbed soft liner of the valve assembly of FIGS. 2 and 3.

FIG. 5 shows a cross-sectional view of a preferred configuration of the liner 46, particularly the soft silicone liner. This liner 46 can be made of many types of elastomer that will conform when force is applied. The silicone liner ribbing 64 will deform under pressure so as to create a better sealing. In order to allow the balloon round tail 42 to exit the housing, a round balloon tail clearance 66 is provided which corresponds with the balloon round tubing exit 56 in the balloon housing 40. The flat balloon tail clearance 68 allows the flat balloon tail 52 to be assembled with minimal bulk. The ribs 64 are a preferred, but non limiting feature of the liner 46. In fact, having an elastomer/soft liner without ribs is still an effective solution to close the gaps between the guide wires/catheters.

Figure 6:
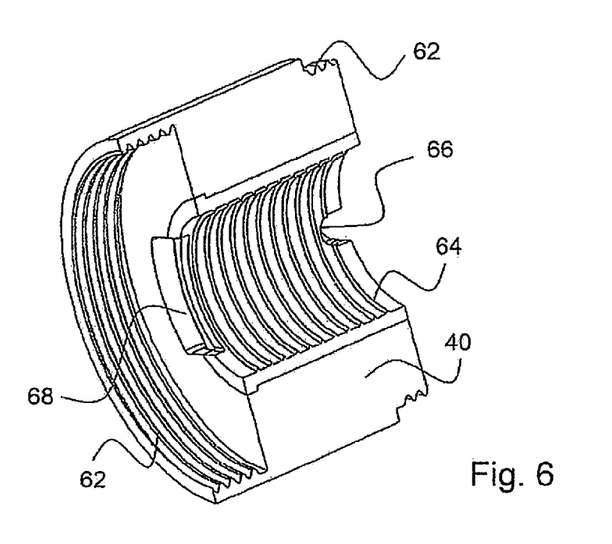
FIG. 6 is an enlarged, cross-sectional view of a balloon housing and assembled ribbed soft liner.

FIG. 6 shows a cross-sectional, perspective view of the balloon housing 40 and the ribbed liner 46 assembly. The clearances 66 and 68 are aligned to the respective flat tail bonding cavity 58 and balloon housing round tubing exit cutout. These cutouts and clearances allow more efficient assembly and use of space within the valve assembly, so as to reduce its overall dimensions.

Figure 7:
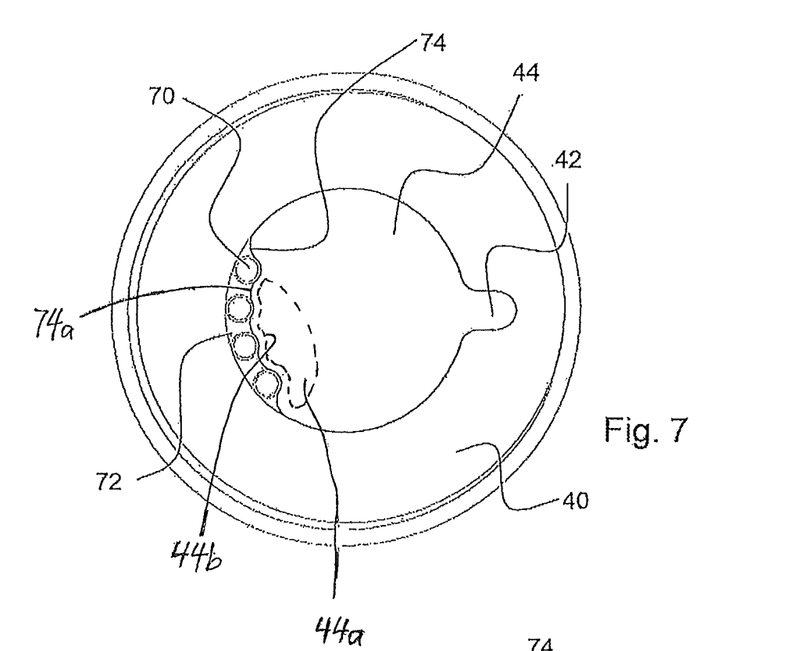
FIG. 7 is an enlarged, cross-sectional view of a balloon housing without soft lining that shows gaps between the guide wires/catheters which are leak paths at moderate pressures.

FIG. 7 shows some details of the sealing with a balloon 44 assembled to the balloon housing 40, without a ribbed liner. The position of the balloon round tail 42 is shown off to the side. The arrangement in FIG. 7 is shown with light/moderate pressure. The single or multiple guide wires/tubing 70 is shown as passing through the access port. The balloon 44 has a balloon wall 74 with an outer surface 74a facing away from the inner surface 44b. The balloon wall 74 is depicted as conforming around the wire to create some closing of the gaps 72 between the guide wires 70.

Figure 8:
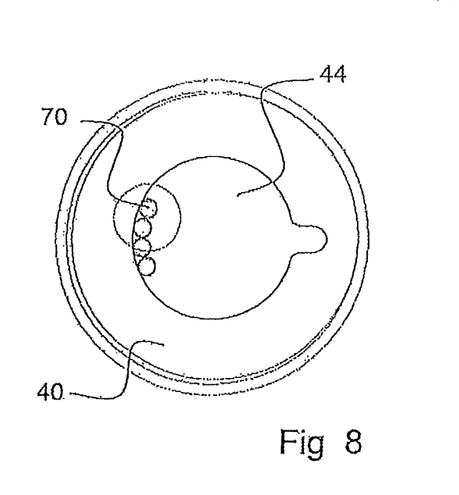
FIG. 8 is an enlarged, cross-sectional view of a balloon housing without soft lining that shows conforming of balloon wall on the side of the guide wires/catheters at a higher pressure than that of FIG. 7.
Figure 8A:
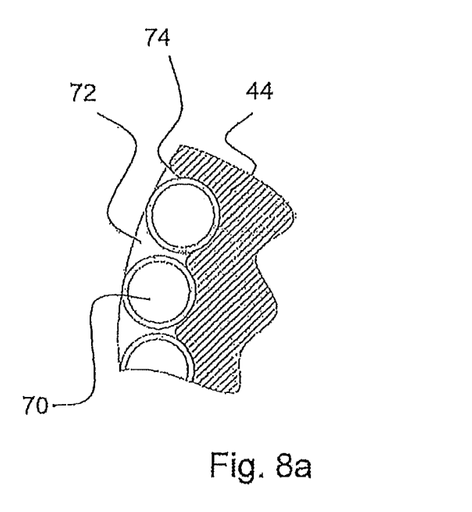
FIG. 8a is an enlarged view of the detail indicated in FIG. 8.

In FIG. 8, the balloon 44 is inflated with more pressure so that the balloon wall 74 can surround and conform more around the guide wire/tubing 70. The higher magnification details of FIG. 8a show the guide wires/tubing 70 and balloon wall 74, which balloon wall is more in conformance with the guide wire/tubing 70. However, a gap 72 from the balloon housing side is still open. The sealing capability has thus increased. However, due the rigidity of the housing 40, a limited gap 72 still persists. This embodiment with a balloon is, however, an improvement over an access port without a balloon 44 seal.

Figure 9:
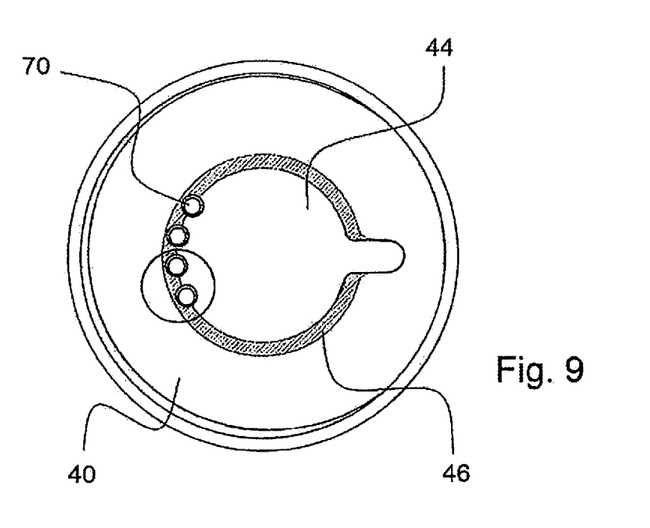
FIG. 9 is an enlarged, cross-sectional view of a balloon housing with ribbed soft lining that shows gaps between the guide wires/catheters filled by soft ribs which minimize leak paths.

In FIG. 9 a preferred embodiment is shown of a valve assembly comprising the balloon housing 40, the soft ribbed liner 46 which is preferably made of silicone, and the balloon 44. The guide wires/tubing 70 are also shown.

Figure 10:
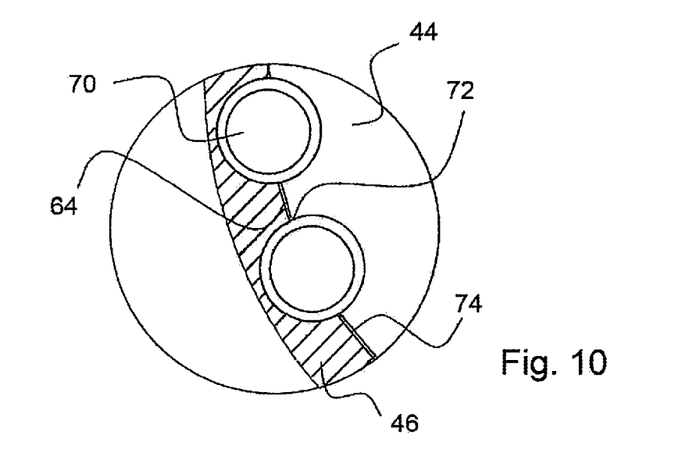
FIG. 10 is an enlarged view of the detail indicated in FIG. 9 showing the balloon housing with ribbed soft lining and pressurized balloon that shows filled gaps between the guide wires/catheters which minimize leak paths.

FIG. 10 shows the magnified detail of the balloon housing with the silicone liner 46 and the inflated balloon 44 which together conform around the guide wire/tubing 70. Even at lower pressure in the balloon 44, the ribbed silicone liner 46 and the balloon wall 74 sandwich the guide wire/tubing therebetween. The softness of the silicone liner 46 and its ribs 64 seal against the guide wire/tubing 70 so as to reduce the gaps 72 to a small size, if not closing them completely. During studies conducted on animals, the bleeding was negligible compared to access ports without the balloon 44 and the silicone liner 46.

Figure 11:
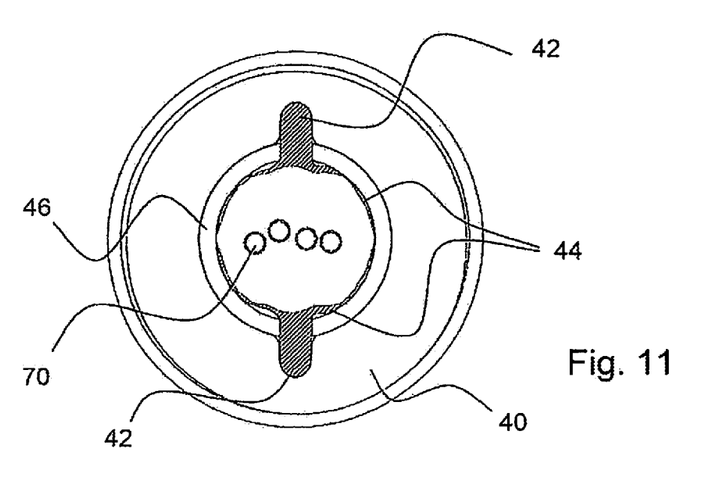
FIG. 11 is an enlarged, cross-sectional view of another embodiment of the valve assembly including two balloons in a housing, in a condition without pressure applied thereto.

FIG. 11 shows another embodiment with deflated dual balloons 44 in the balloon housing 40. The balloon round tails 42 are shown positioned opposite to each other on the balloon housing 40. This configuration is shown with the ribbed silicone liner 46, although in this embodiment the ribbed silicone liner 46 is not essential since the sealing of the gaps between the guide wires/tubing is achieved by the interaction of the two balloons 44. The guide wire/tubing 70 is shown going through the centre of the device.

Figure 12:
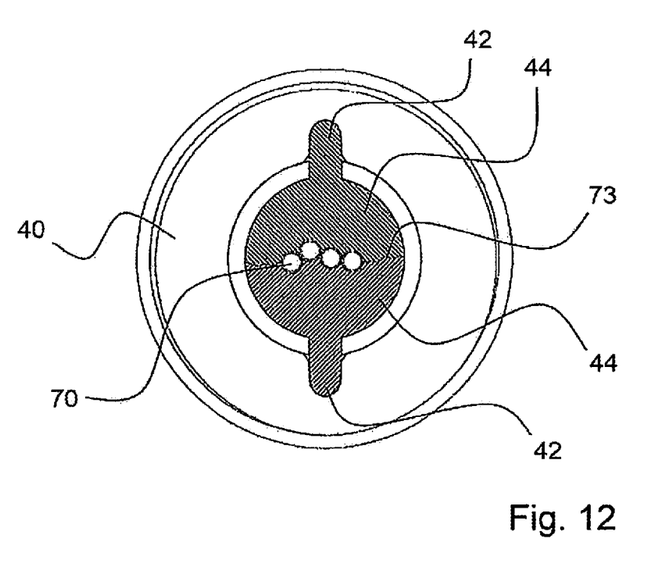
FIG. 12 is an enlarged, cross-sectional view showing the embodiment of FIG. 11 showing the housing with the two balloons pressurized so as to close leak paths.

FIG. 12 shows the inflated dual balloon configuration. The guide wire/tubing 70 is surrounded by the inflated balloons 44 and the balloon walls 73 close around the guide wire/tubing 70 to make the seal.

Figure 13:
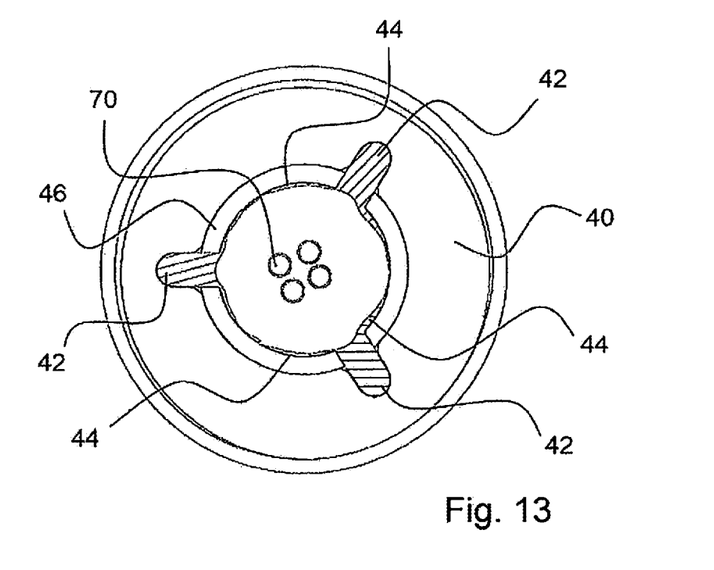
FIG. 13 is an enlarged, cross-sectional view of yet another embodiment of the valve assembly including three balloons in a housing, in a condition without pressure applied thereto.

FIG. 13 shows another embodiment where three balloons 44 are used inside the balloon housing 40. In this figure, the three balloons 44 are in a deflated state where the balloon round tubings 42 are positioned at 120 degrees apart in the balloon housing 40. The ribbed silicone liner 46 is shown, however, as with the dual balloon embodiment described above, the liner 46 is not essential since the sealing of the gaps between the guide wires/tubing is achieved by the interaction of the three balloons 44. The guide wire/tubing 70 extend through the middle/centre of the device.

Figure 14:
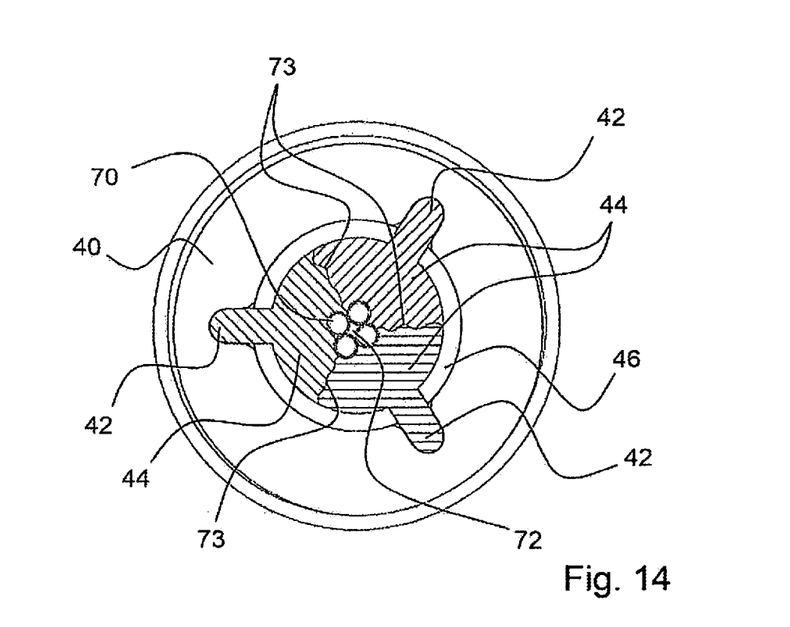
FIG. 14 is an enlarged, cross-sectional view showing the embodiment of FIG. 13 showing the housing with the three balloons pressurized so as to close leak paths.

FIG. 14 shows the same three balloon embodiment of the previous figure, with the balloons 44 inflated so as to close the gap 72. The balloon walls 73 are touching each other thus creating an effective seal which encloses the guide wire/tubing 70.

Figure 15:
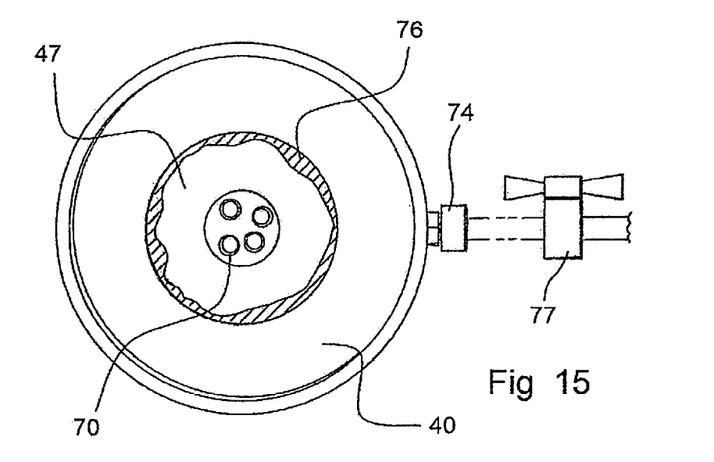
FIG. 15 is an enlarged, cross-sectional view of yet another embodiment of the valve assembly including a high distention elastomer balloon in a housing, in a condition without pressure applied thereto, also showing an inflation port.

FIG. 15 is another embodiment where an elastic balloon 76 is bonded/assembled airtight to the balloon housing 40 both distally and proximally. This elastic balloon 76 is inflated using an inflation port 74. The inflation port 74 has a stopcock 77 attached to lock the pressure once the balloon 76 is inflated. The large silicone seal 47 is shown, with the guide wire/tubing going through its centre.

Figure 16:
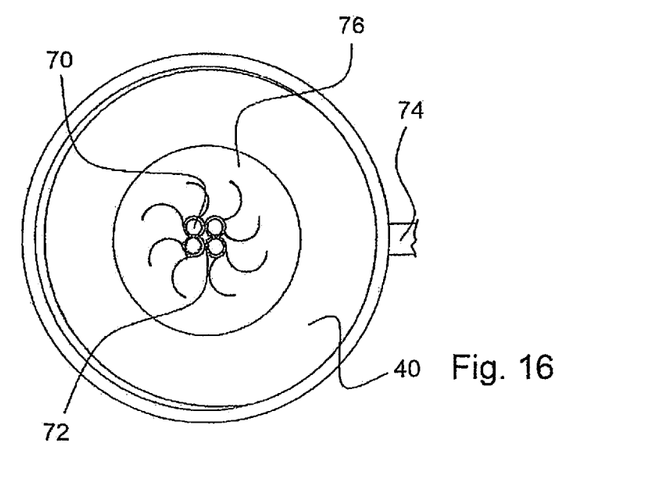
FIG. 16 is an enlarged, cross-sectional view showing the embodiment of FIG. 15 showing the elastomer balloon in the housing after pressurization.

FIG. 16 schematically shows the elastic balloon 76 which has been inflated using the inflation port 74. The inflated balloon 76 closes the centre around the guide wire/tubing 70 from outside into the centre. The gap 72 closes although limited clearance remains which is defined by the guide wire/tubing 70 geometry. A remaining small gap 72 can potentially still leak, however, the leakage is reduced significantly compared to the configuration without this elastic balloon 76.

Figure 17:
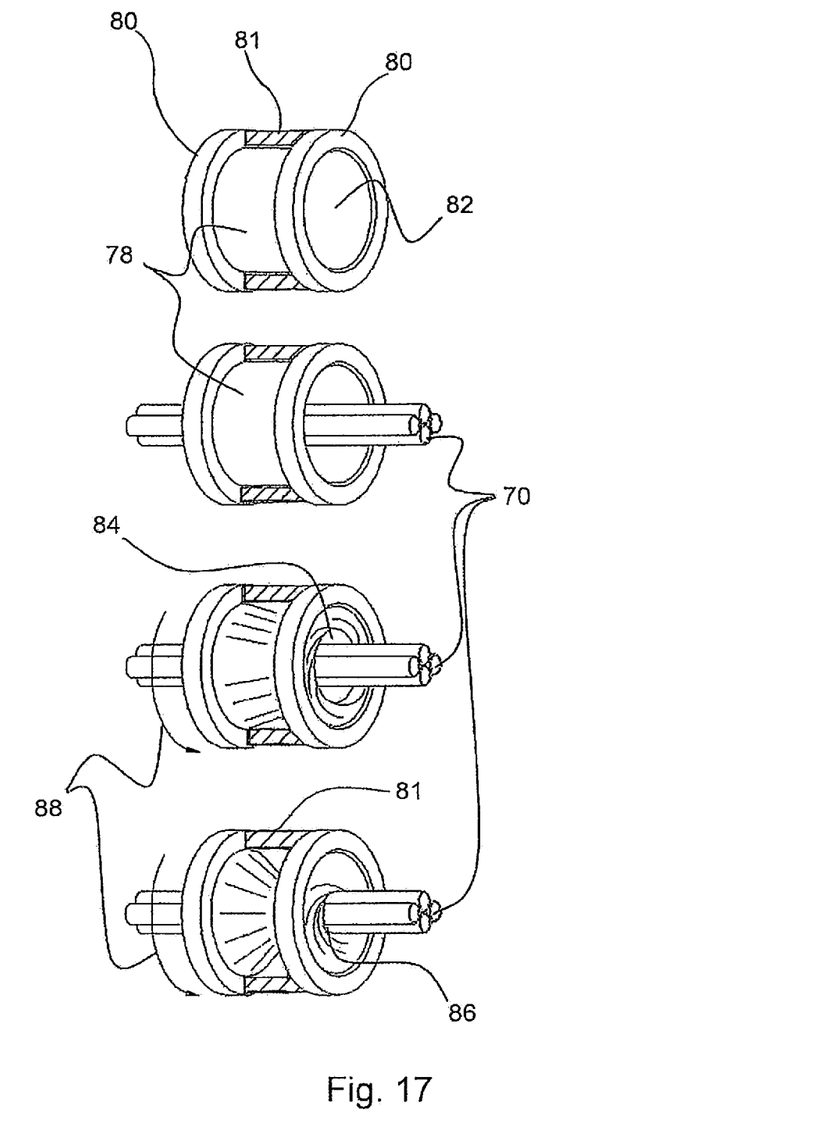
FIG. 17 is yet another embodiment showing an iris type of sealing showing each stage of sealing with and without guide wire/tubing/catheter at various stages.

FIG. 17 shows another embodiment. This embodiment comprises an iris type of seal which serves the same purpose as the balloon(s) of the previous embodiments. A flexible iris tubing 78 is assembled with its ends connected to a couple of iris rings 80. The flexible iris tubing 78 is inserted into a tubular housing 81. One or both of the iris rings 80 are free to rotate about the longitudinal axis of the flexible iris tubing 78. The centre hole 82 through the iris receives the guide wire/tubing 70. As the ring/rings 80 rotate opposite to each other as shown by arrows 88, the iris tubing 80 closes and the through hole 82 closes as shown by reference numeral 84. Once the rotation of the iris rings approaches approximately 180 degrees, the through hole 86 completely closes so as to create a seal around the guide wire/tubing 70. This embodiment reduces the leak through the valve significantly and has a big advantage over the standard dual seal access ports shown on FIG. 1.

In general terms, a standard dual valve configuration such as the one shown in FIG. 1 does not seal when there are guide wires/tubing 70 through the standard elastic valves, because the guide wires/tubing 70 prevent the proper closing of such standard elastic valves. Using the embodiments described above, which incorporate a singular balloon, multiple balloons, an elastic balloon or an iris type of seal, sealing effectiveness is increased tremendously.

The invention claimed is:

1. A valve assembly with sealing capability for instruments and/or guide wires for use as an access/tool port, said valve assembly comprising:
 a valve housing having a through hole therein;
 a cannula attached to said valve housing; and
 a sealing arrangement disposed within said valve housing for sealing said through hole thereof, said sealing arrangement comprising at least one balloon having an inner surface and an outer surface facing away from said inner surface and towards an adjacent wall of said valve housing defining at least part of said through hole, said balloon having an interior chamber, said interior chamber being defined solely by said at least one balloon and communicating with an inflation source, said sealing arrangement having a non-sealed configuration in which at least one generic device is insertable into, or removable from, said through hole and a sealed configuration in which said at least one balloon is inflated and expanded within said through hole to reduce a size thereof, wherein in said sealed configuration said outer surface of said at least one balloon seats against and conforms to the at least one generic device inserted within said through hole to seal said through hole, said outer surface of said at least one balloon and said adjacent wall of said valve housing sandwiching the at least one generic device therebetween in said sealed configuration.

2. The valve assembly of claim 1, wherein when said at least one balloon is inflated and expanded within said through hole in said sealed configuration of said sealing arrangement, said size of said through hole is reduced to an area defined primarily between said outer surface of said at least one balloon and said adjacent wall of said valve housing, and the at least one generic device is located within said area of said through hole when inserted therein.

3. The valve assembly of claim 1, wherein when said at least one balloon is inflated in said sealed configuration of said sealing arrangement, said adjacent wall of said valve housing is in contacting relation with the at least one generic device when inserted within the through hole.

4. The valve assembly of claim 1, wherein said at least one balloon comprises a tail in communication with said interior chamber for inflation or deflation of said at least one balloon, said tail being disposed eccentrically with respect to a longitudinal axis of said at least one balloon.

5. The valve assembly of claim 1, wherein said at least one balloon comprises a sealed tail disposed to anchor said at least one balloon to said valve housing, said sealed tail being disposed eccentrically with respect to a longitudinal axis of said at least one balloon.

6. The valve assembly of claim 1, further comprising a deformable liner disposed in said through hole of said valve housing and including said adjacent wall of said valve housing, said liner cooperating with said outer surface of said at least one balloon to seal around a periphery of the at least one generic device in said sealed configuration of said sealing arrangement.

7. The valve assembly of claim 6, wherein said liner is annular and comprises soft annular ribs distributed along a length of said liner along an inner surface thereof.

8. The valve assembly of claim 1, wherein in said sealed configuration of said sealing arrangement a first part of said outer surface of said at least one balloon seats against and conforms to the at least one generic device inserted within said through hole and along with said adjacent wall of said valve housing sandwiches the at least one generic device therebetween, said adjacent wall being a first adjacent wall, and a second part of said outer surface of said at least one balloon expands against a second adjacent wall of said valve housing defining part of said through hole, said first and second adjacent walls both forming part of an annular wall of said valve housing defining said through hole.

9. The valve assembly of claim 1, further comprising an elastic valve member disposed in said valve housing for sealing said through hole when the at least one generic device is not inserted within said through hole or for additionally sealing said through hole in conjunction with said sealing arrangement when the at least one generic device is inserted within said through hole.

10. The valve assembly of claim 1, wherein said at least one balloon comprises a sealed tail integrally formed with said at least one balloon and projecting away from said outer surface thereof, said valve housing defining therein a mounting area at which said sealed tail is fixed to anchor said at least one balloon to said valve housing.

* * * * *